(12) United States Patent
Abraham-Fuchs et al.

(10) Patent No.: US 7,932,082 B2
(45) Date of Patent: Apr. 26, 2011

(54) DEVICE AND METHOD FOR EXTRACTING A SMEAR SAMPLE

(75) Inventors: Klaus Abraham-Fuchs, Erlangen (DE); Thomas Ehben, Weisendorf (DE); Walter Gumbrecht, Herzogenaurach (DE); Peter Paulicka, Erlangen (DE); Sebastian Schmidt, Erlangen (DE); Manfred Stanzel, Erlangen (DE); Christian Zilch, Leipzig (DE)

(73) Assignee: Siemens Aktiengesellschaft, Munich (DE)

( * ) Notice: Subject to any disclaimer, the term of this patent is extended or adjusted under 35 U.S.C. 154(b) by 1197 days.

(21) Appl. No.: 11/599,424

(22) Filed: Nov. 15, 2006

(65) Prior Publication Data

US 2008/0193926 A1    Aug. 14, 2008

(30) Foreign Application Priority Data

Nov. 17, 2005   (DE) .......................... 10 2005 054 924

(51) Int. Cl.
*C12M 1/26* (2006.01)
*C12M 3/00* (2006.01)

(52) U.S. Cl. ... 435/309.1; 435/6; 435/288.5; 435/288.6; 435/304.1; 435/305.1

(58) Field of Classification Search .......... 435/6, 288.5, 435/288.6, 309.1, 304.1, 305.1, 297.1, 297.2, 435/283.1
See application file for complete search history.

(56) References Cited

U.S. PATENT DOCUMENTS

| | | | |
|---|---|---|---|
| 4,774,962 A | 10/1988 | Hebel et al. | |
| 4,877,036 A | 10/1989 | Saint-Amand | |
| 5,078,968 A * | 1/1992 | Nason | 422/58 |
| 5,268,148 A | 12/1993 | Seymour | |
| 6,180,395 B1 | 1/2001 | Skiffington et al. | |
| 6,303,081 B1 | 10/2001 | Mink et al. | |
| 6,416,715 B1 | 7/2002 | Gambert et al. | |
| 6,548,018 B2 * | 4/2003 | DiCesare et al. | 422/52 |
| 2001/0041357 A1 * | 11/2001 | Fouillet et al. | 435/91.1 |
| 2002/0173047 A1 | 11/2002 | Hudak et al. | |
| 2003/0129673 A1 | 7/2003 | Schwarz et al. | |
| 2003/0129767 A1 | 7/2003 | Bautista et al. | |
| 2004/0022687 A1 | 2/2004 | Wuske et al. | |
| 2004/0057876 A1 | 3/2004 | Wuske et al. | |
| 2004/0161788 A1 | 8/2004 | Chen et al. | |
| 2004/0189311 A1 | 9/2004 | Glezer et al. | |
| 2004/0209266 A1 * | 10/2004 | Squirrell | 435/6 |
| 2004/0214316 A1 * | 10/2004 | O'Connell | 435/309.1 |

(Continued)

FOREIGN PATENT DOCUMENTS

DE    36 32 303 C2    4/1995

(Continued)

OTHER PUBLICATIONS

Great Britain Search Report dated Mar. 15, 2007.

(Continued)

*Primary Examiner* — Walter D Griffin
*Assistant Examiner* — Shanta G Doe
(74) *Attorney, Agent, or Firm* — Harness, Dickey & Pierce, P.L.C.

(57) ABSTRACT

A device is disclosed for extracting a smear sample. The device includes a cavity, into which a sample carrier carrying a smear sample can be introduced. Liquid can be introduced into the cavity through at least one liquid feed connected to the cavity, and the liquid can be removed from the cavity through at least one liquid discharge connected to the cavity.

32 Claims, 6 Drawing Sheets

U.S. PATENT DOCUMENTS

| | | |
|---|---|---|
| 2005/0019757 A1 | 1/2005 | Stolarchuk |
| 2005/0047963 A1 | 3/2005 | Safar et al. |
| 2005/0059165 A9 | 3/2005 | Davis et al. |
| 2005/0084842 A1* | 4/2005 | O'Connor .......................... 435/4 |

FOREIGN PATENT DOCUMENTS

| | | |
|---|---|---|
| DE | 197 48 331 C1 | 1/1999 |
| DE | 198 09 702 A1 | 9/1999 |
| DE | 103 28 984 B4 | 4/2005 |
| DE | 101 53 925 B4 | 8/2005 |
| DE | 10 2004 009 985 A1 | 9/2005 |
| EP | 1 338 886 A1 | 8/2003 |
| EP | 1 553 394 A1 | 7/2005 |
| EP | 1 346 692 B1 | 6/2006 |
| GB | 2422664 A | 8/2006 |
| WO | WO 95/02996 | 2/1995 |
| WO | WO 95/30484 | 11/1995 |
| WO | WO 01/81915 A1 | 11/2001 |
| WO | WO 03/064046 A1 | 8/2003 |
| WO | WO 2004/061418 A2 | 7/2004 |

OTHER PUBLICATIONS

German Office Action.

* cited by examiner

DEVICE AND METHOD FOR EXTRACTING A SMEAR SAMPLE

PRIORITY STATEMENT

The present application hereby claims priority under 35 U.S.C. §119 on German patent application number DE 10 2005 054 924.1 filed Nov. 17, 2005, the entire contents of which is hereby incorporated herein by reference.

FIELD

The present invention generally relates to a device and/or a method for extracting a smear sample.

BACKGROUND

For the analysis of biological, medical or chemical samples, smear samples are also used besides liquid samples, for example blood samples. In this case, for example, a sterile cotton swab is wiped over a body site to be analyzed, for example the oral mucosa, so that a part of the desired sample material remains adhering to the cotton swab or partially impregnates it. In forensic molecular biology, for example, saliva samples are often taken in the form of smears in order to identify a culprit through a DNA analysis.

In order to make the smear sample placed on the cotton swab or a comparable sample carrier available for further analysis, extraction of the smear sample from the sample carrier is necessary. In known methods, this has previously been done manually. In the case of a cotton swab, for example, a stick carrying the cotton bud is broken off close to the cotton bud for this purpose. To this end, there is generally a weakened fracture site on the stick. The cotton bud is subsequently put into a vessel such as an Eppendorf tube filled with a carrier liquid, for example a salt solution, shaken ("vortexed") and centrifuged at a high speed. In this way, the smear sample is released from the cotton bud and is available dissolved or suspended in the carrier liquid. By means of this carrier liquid, it can be delivered for further processing and thereby analyzed.

US 2003/0129767 A1 discloses a test unit in which a cotton stick with a smear sample can be introduced into a container. After supplying a solution liquid, the container is introduced into a test strip so that the dissolved smear sample can enter inside the test unit. The smear sample mixed with reagents is transported by capillary forces into a detection zone, on which the result of the test can be read.

Biochips are increasingly gaining importance for the analysis of samples. Using biochips, for example, it is possible to detect the concentration or presence of biomolecules, for example nucleic acid fragments or proteins, in biological or medical samples. Biochip systems are based, for example, on a multicomponent system in which the biochip itself is arranged in a single-use unit (cartridge). The cartridge is inserted into a reader and controller in order to carry out the analysis. The reagents needed for carrying out the analysis may be stored in the cartridge in a dry or liquid form or in the reader.

If smear samples are intended to be processed using such biochip systems, then manual release as described above is necessary since in many biochip systems only liquid samples can be processed directly. This is an impediment to the otherwise of fully integrated analysis opportunity offered by biochips.

SUMMARY

At least one embodiment of the present invention provides a device and/or a method for extracting a smear sample, by which the smear sample can be substantially extracted automatically.

According to at least one embodiment, the device according to the invention comprises the following features:
- a cavity, into which a sample carrier carrying a smear sample can be introduced,
- at least one liquid feed connected to the cavity, through which liquid can be introduced into the cavity and
- an interface to a microfluidic system, into which liquid can be transferred.

A device designed in this way has the advantage that the smear sample on the sample carrier merely has to be introduced into the cavity, whereupon a flushing liquid can automatically be introduced into the cavity via the liquid feed. The smear sample is released from the sample carrier by the flushing liquid, and can be removed again from the cavity through the liquid discharge. Automatic extraction of the smear sample is possible by use of this device, manual working steps being substantially avoided.

In a particularly example embodiment of the invention, the device comprises an interface to a microfluidic system, into which liquid can be transferred. This is advantageous particularly for biochip systems which operate with a cartridge based on a microfluidic system. The smear sample can be transferred automatically into the microfluidic system. A device configured in this way obviates both manual extraction and manual transfer of the dissolved smear sample into the cartridge.

In an advantageous version of an embodiment of the invention, the liquid feed and/or the liquid discharge comprise at least one microchannel. In this case, the device is simple to configure in a miniaturized form and easily coupled to the microfluidic system of the cartridge. The liquid feed and the liquid discharge may be connected directly to the microfluidic system or may even be part of this system. Flushing liquid to be fed into the cavity may, for example, be supplied from the microfluidic system.

In an advantageous embodiment of the invention, the cavity comprises a reception opening for the sample carrier, which can be sealed liquid-tightly by a stopper. In the case of cotton swabs, for example, this has the advantage that the part of the stick carrying the cotton can be introduced through the reception opening into the cavity, and then broken off at a weakened fracture site. The cavity is sealed water-tightly by the stopper, so that the device may for example be operated in a horizontal position without affecting the sample carrier. Particularly in cartridge-based analysis systems, the cartridge is generally inserted in a horizontal form into a reader. In this case, it is necessary to prevent the sample carrier from falling out of the cavity or flushing liquid from being able to escape. This is achieved by a water-tight stopper.

In an advantageous embodiment of the invention, the reception opening is likewise sealable germ-tightly by the stopper. This has the advantage of substantially preventing contamination when handling the device. For example, it is no longer necessary to use gloves after introducing the sample carrier and sealing the cavity.

In a particularly advantageous embodiment of the invention, the stopper is designed so that the cavity is automatically sealed after introducing the sample carrier. This may, for example, be achieved using a stopper driven by an electric motor. In this way, it is not possible to forget to close the cavity before processing the sample further. This reduces the susceptibility to error and the risk of contamination.

In a particularly advantageous embodiment of the invention, the liquid feed comprises at least one liquid reservoir which can be connected at least temporarily to the cavity and from which, when it is connected to the cavity, liquid can be introduced into the cavity. Forming the liquid reservoir inside the device has the advantage that it increases the flexibility of its use. The extraction of the smear sample may for example take place directly at the site of the sampling, even if an analyzer is not yet available. The previously extracted sample provided in liquid form may, for example, be transferred later into an analyzer in a laboratory. Further to this, the various configurations of the device make it possible to adapt to different types of sample carriers. For example, different liquids may be required for cotton-based sample carriers than for other sample carriers. By different configurations of the device, for example, various smear samples may be extracted and transferred into a universal analysis system.

In a particularly advantageous configuration of an embodiment of the invention, the cavity comprises an inlet opening and an outlet opening, which are fluidically connected respectively to the liquid feed and the liquid discharge. The outlet opening and the inlet opening are in this case arranged so that, when the sample carrier is introduced, a maximally large section of the sample carrier lies between the inlet opening and the outlet opening. This ensures that as much sample material as possible is released from the sample carrier when the cavity is flushed through with flushing liquid.

In an advantageous embodiment of the invention, the cavity is matched to a shape and size of the sample carrier so that, when the sample carrier is introduced into the cavity, between a wall of the cavity and the sample carrier there is a spacing dimensioned such that liquid can be transported past the sample carrier from the inlet opening to the outlet opening. This is advantageous particularly for sample carriers made of a solid material, for example rubber, since it ensures that the sample carrier does not seal the outlet opening or the inlet opening, and that liquid can be transported past the sample carrier. It also ensures that the liquid must flow past the sample carrier, so that it can release the sample from the sample carrier. This is advantageous particularly for types of sample carriers in which the sample mainly lies on its surface.

In an advantageous configuration of an embodiment of the invention, at least one holding part is arranged in the cavity. This prevents the sample carrier from being able to move in the cavity after it has been introduced. Thus, the sample carrier cannot fall out of the cavity before it is sealed. Furthermore, for example, the aforementioned spacing between the wall of the cavity and the sample carrier is readily ensured by the holding part. It is therefore possible to achieve optimal flushing of sample material from the surface of the sample carrier. It is moreover readily possible to prevent the sample carrier from sealing the outlet opening, for example.

In an advantageous configuration of an embodiment of the invention, the holding part is essentially shaped according to the sample carrier and the sample carrier can be inserted into the holding part. The holding part has a spacing from the wall of the cavity dimensioned so that liquid can travel from the inlet opening to the outlet opening, the holding part comprising openings which facilitate contact between the liquid and the introduced sample carrier. This is a configuration of the holding part which is particularly simple to implement, so that the spacing between the sample carrier and the wall of the cavity is readily ensured. The openings constantly ensure that liquid can reach the surface of the sample carrier, such that the smear sample lying on the surface can enter solution.

In an advantageous configuration of an embodiment of the invention, the holding part comprises a sieve-like structure. By virtue of the holding part configured in this way with many openings, it is readily possible to ensure maximal contact between the surface of the sample carrier and the liquid flowing past it. The effect achieved by this is that a maximal proportion of the smear sample can be released from the sample holder by the flushing liquid.

In an advantageous configuration of an embodiment of the invention, the holding part is arranged in the reception region while being designed so as to prevent parts of the sample carrier, which carry the smear sample, from being removed from the cavity. This is advantageous particularly for cotton swabs which comprise a weakened fracture site, so that the part carrying the smear sample always remains in the cavity after it has been introduced, and the process of breaking the stick is assisted.

A device such that the holding part comprises at least one recess, converging acutely essentially in the insertion direction of the sample carrier, is furthermore advantageous. This recess, acting as a retaining hook, may for example release the cotton from the stick or assist the breaking process when the cotton stick is being retracted. It straightforwardly ensures that the cotton, and therefore the smear sample, can no longer be removed from the cavity.

In an advantageous configuration of an embodiment of the invention, the cavity is matched to a shape and size of the sample carrier so that, when the sample carrier is introduced into the cavity, between a wall of the cavity and the sample carrier there is a spacing dimensioned such that the liquid can travel from the inlet opening to the outlet openings only by passing through the sample carrier. This is advantageous for example with cotton swabs as sample carriers since in this case the majority of the smear sample lies not on the surface of the sample carrier but inside it. This is the case particularly when cotton buds are impregnated. If the cotton is pressed against the outlet opening during insertion into the cavity, for example, then the liquid can reach the outlet opening essentially only by passing through the cotton.

In order to increase the permeated volume of the cotton, the cavity may, in at least one embodiment, advantageously comprise a taper in the region of the outlet opening. This ensures that the sample carrier is in contact with the wall of the cavity in the region of the outlet opening, so as to prevent flushing liquid from flowing past it.

In a particular example embodiment of the invention, a separating unit which subdivides the cavity into at least two sub-cavities is arranged in the cavity. In each of the subspaces, there is an inlet opening connected to the liquid feed. The reception opening and the outlet opening lie in different subspaces. The separating unit comprises an access opening, through which the sample carrier can be introduced at least partially into the sub-cavity with the outlet opening, the sample carrier being at least partially closed essentially with a form fit by the access opening. Liquid from the cavity with the reception opening can therefore be transported to the outlet opening only by passing through the sample carrier. At the same time, in the sub-cavity in which the liquid outlet opening lies, the surface of the sample carrier is flushed as well as possible so as to release the smear sample more efficiently. This has the advantage that on the one hand the sample carrier is held by the separating unit, and on the other hand it is washed by two liquid streams so that the smear sample can be released from the sample carrier as efficiently as possible. The separating unit is configured, for example, as a sealing ring made of rubber.

In an advantageous example embodiment of the invention, the outlet opening can be connected outside the cavity selectively to the inlet opening or the liquid discharge. This has the advantage that liquid already flushed through the cavity, which already contains a part of the smear sample, can be transported back into the cavity via the inlet opening. It is thus possible to release a larger proportion of the smear sample from the sample carrier. This is advantageous particularly when there are small sample quantities on the sample carrier.

In an advantageous configuration of an embodiment of the invention, the outlet opening is connected to a channel system, the channel system comprising at least one valve via which the outlet opening can be connected selectively to the inlet opening or the liquid discharge. This is a particularly simple and inexpensively producible version of an embodiment of the invention to facilitate multiple flushing through the cavity.

In the region of the outlet opening, it is furthermore advantageous for the cavity to comprise a taper shaped so that, when the sample carrier is introduced, the latter is mechanically deformed such that the smear sample at least partially escapes. This is advantageous for example in the case of deformable sample carriers, such as cotton swabs, since here the smear sample is already extracted at least partially when inserting the sample carrier. Through the supply of liquid, this sample can be transported out of the cavity without more flushing processes being necessary.

A version of an embodiment of the invention such that treatment reagents for the sample are stored in the cavity is particularly advantageous. These may, for example, be reagents for carrying out a lysis by which cell walls of cells contained in the sample are broken up and the target molecules contained in them are released, for example DNA or proteins. Directly during the extraction, initial processing steps can thus be carried out in the sample which simplify and accelerate subsequent processing and analysis of the sample. The treatment reagents may be stored in a dry form in the cavity, or in a liquid form, for example in the liquid reservoir.

It is furthermore advantageous for the treatment reagents to comprise devices/objects/things for binding at least parts of the sample. These may, for example, be configured as functionalized magnetic beads, by which smear sample parts to be analyzed can straightforwardly be bound so that they can be removed from the device and, for example, transferred via the microfluidic interface into an analyzer. The magnetic beads are functionalized so that they can bind the target molecules.

The device thus advantageously comprises at least one magnet unit, by which the magnetic beads can be moved. In this way, for example, merely the parts to be analyzed can be removed from the device through the liquid discharge by way of the magnetic beads, and made available for the further analysis. Additional washing steps, possibly to be carried out in the scope of the analysis in order to purify the sample, can thus substantially be avoided.

The method according to at least one embodiment of the invention comprises the following method steps:
  providing a device,
  introducing the sample carrier into the cavity of the device,
  introducing liquid into the cavity through the liquid feed,
  releasing at least parts of the smear sample from the sample carrier by the liquid, and
  at least partially removing the liquid and the smear sample through the liquid discharge.

The method according to at least one embodiment of the invention offers a simple and automated method for extracting the smear sample from the sample carrier. Manual working steps can thereby be substantially avoided and, for example, the introduction of smear samples into microfluidic systems of biochip-based cartridge systems is facilitated.

BRIEF DESCRIPTION OF THE DRAWINGS

Further advantages of the invention will be found in conjunction with the example embodiments explained below with reference to the appended drawings.

In the figures.

DETAILED DESCRIPTION OF THE EXAMPLE EMBODIMENTS

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

The invention will be explained below with the aid of several example embodiments. In this case, a reception device for a cotton swab in stick form will be discussed by way of example. Corresponding configurations for other sample carriers are to be embodied accordingly. In principle, the main requirement of the device according to an embodiment of the invention is that a cotton bud of the cotton swab should be flushed as fully as possible with a flushing liquid, so that a maximal quantity of the smear sample from a maximally large volume of the cotton bud is received by the flushing liquid and is thus made available for subsequent treatment or analysis.

A particular advantage of the device according to an embodiment of the invention and its preferred versions is that it can also be integrated into an analysis system, for example inside a cartridge, and is thus connected directly to the microfluidic system of the cartridge. The example embodiments described below present the device according to the invention as part of such a cartridge by way of example.

Figure 1:
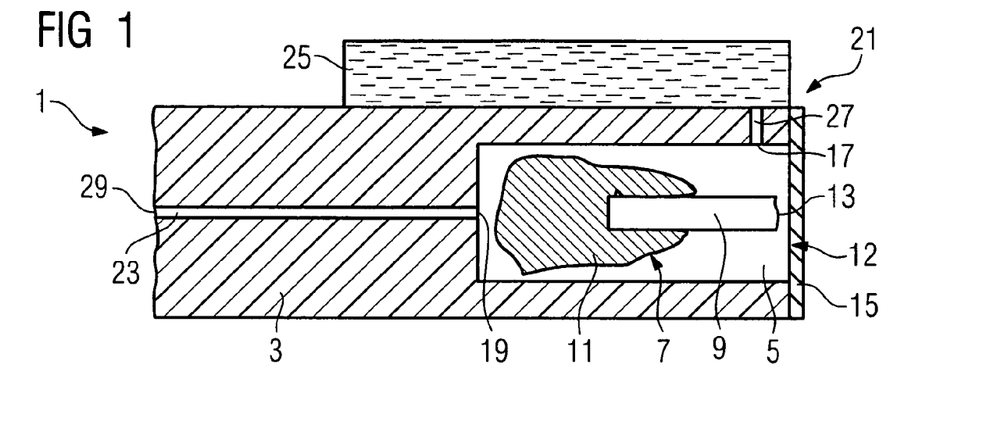
FIGS. 1 to 17 show various embodiments of the invention.

FIG. 1 thus represents only a detail of a cartridge 1, in which full analysis of a smear sample can be carried out. The cartridge 1 consists essentially of a plastic body 3 having a microfluidic system, only parts of which are shown here. A cavity, which constitutes a reception chamber 5 for a sample carrier 7, is formed in the cartridge 1. Here, the sample carrier 7 is embodied in the form of a cotton bud 11 fastened on a carrier stick 9. The sample carrier 7 is introduced through a reception opening 12 into the reception chamber 5, whereupon the carrier stick 9 is broken off at a weakened fracture site 13 so that only a short stub of the carrier stick 9 with the cotton bud 11 remains in the reception chamber 5. The reception chamber 5 is sealed water- and germ-tightly by a rubber lid 15. It comprises an inlet opening 17 and an outlet opening 19, which are respectively connected to a liquid feed 21 and a liquid discharge 23. The liquid feed 21 comprises a liquid reservoir 25, which is connected directly via a microchannel 27 to the inlet opening 17.

Devices/objects/things for transporting the flushing liquid contained in the liquid reservoir 25 through the microchannel 27 to the inlet opening 17, and thus into the reception chamber 5, are not represented. Known solutions for transporting liquid through microchannels can be used here, for example piston pumps or plungers. When the flushing liquid is pumped into the reception chamber 5, it flushes around and through the cotton bud 11, so that the smear sample lying on the cotton bud 11 dissolves in the flushing liquid and is thus transported out of the reception chamber 5 with the flushing liquid via a microchannel 29. The end of the microchannel 29 may for example be followed by a treatment chamber for the sample, which is treated therein for a subsequent analysis.

In the case of a device operating separately from the analysis system, it would be necessary to provide an interface here by which the dissolved smear sample can be transferred into the analysis system. This could, for example, be a cannula connected to the liquid discharge 23. A separate analysis system could, for example, comprise an opening which is sealed by a membrane or a septum. In order to transfer the dissolved smear sample into the analysis system, the membrane or the septum is pierced by the cannula so that the device is fluidically connected to the analysis system. The smear sample is thus available for further processing, for example cell disintegration with subsequent PCR and DNA detection by a biochip. Other known interfaces could alternatively be used, such as so-called "Luer" plug connections or "Luer-lock" bayonet connections.

Since the cartridge 1 is inserted in a horizontal position into a reader (which is not represented here), it is important to seal the reception chamber 5 by the rubber lid 14 at the very latest when the flushing liquid is introduced into the reception chamber 5. A correspondingly designed sealing mechanism may thus be a pressure mechanism, for example, which is triggered by introducing the cotton bud 11 into the reception chamber 5 or by breaking the carrier stick 9 and makes the rubber lid 15 fold shut as soon as the broken stub of the support stick 9 is retracted from the reception chamber 5. The sealing mechanism may also be triggered by inserting the cartridge into the reader, or by the start of introducing the liquid into the reception chamber.

For sample carriers with a denser consistency, for example rubber carriers, the flow pressure of the flushing liquid is sometimes insufficient to permeate the sample carrier. In this case, it is necessary for as much sample material as possible to be washed away from the surface of the sample carrier. It is necessary to ensure that the introduced sample carrier does not seal the outlet opening 19 in this case, since otherwise flushing liquid with released sample could no longer be transported out of the sample reception chamber 5.

Figure 2:
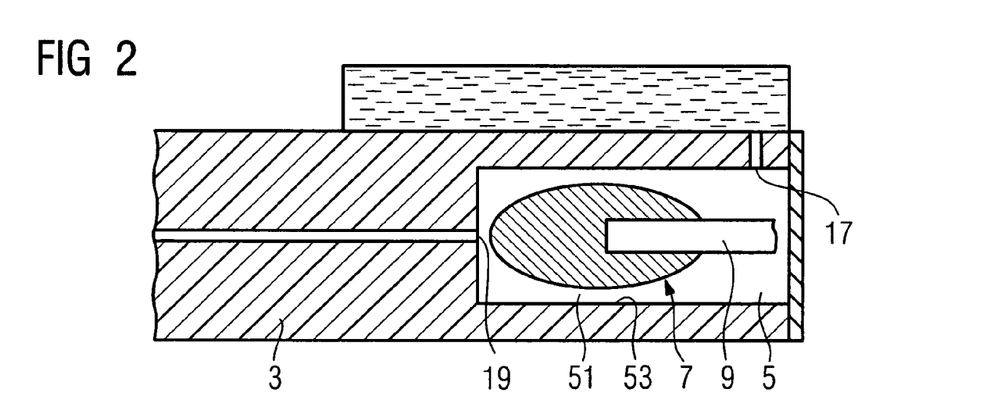

A correspondingly refined device is shown in the example embodiment in FIG. 2. In the example shown, the sample carrier 7 has an oval shape with a comparatively denser consistency. The sample lies primarily on the surface of the sample carrier 7. The reception chamber 5 has a correspondingly adapted shape so that, even when the sample carrier 7 is introduced, a gap 51 still remains between the wall 53 of the reception chamber 5 and the sample carrier 7. This ensures that a liquid flow from the inlet opening 17 around the surface of the sample carrier 7 to the outlet opening 19 is constantly guaranteed. The inlet opening 17 is arranged in the front part of the reception chamber 5, as viewed in the insertion direction of the sample carrier 7, while the outlet opening 19 is arranged in the rear part. The effect achieved by this is that the flushing liquid can flow past a maximally large surface of the sample carrier 7. As much sample substance as possible is received by as little flushing liquid as possible, in a volume of the reception chamber 5 which is as small as possible.

Figure 3:
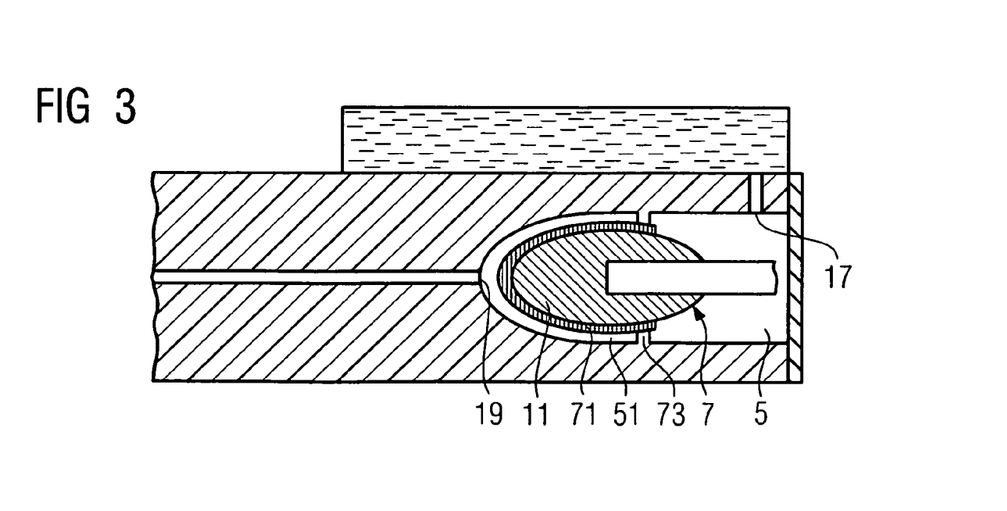

Another improved embodiment is shown in FIG. 3. Here, a holding part configured as a sieve 71, into which the sample carrier 7 is inserted, is additionally arranged in the reception chamber 5. The sieve 71 is fastened to the wall 51 of the reception chamber 5 by way of struts 73, so that liquid transport is possible through between the struts 73. Owing to the sieve 71, the flushing liquid which flows around the sieve 71 has the opportunity to release a large part of the smear sample from the surface of the sample carrier 7 and remove it from the reception chamber 5 via the outlet opening 19. Instead of the sieve 71, it is also possible to fit spacer pins or combs which keep the sample carrier 5 at a distance from the wall 51 in the reception chamber. In the case of a cotton bud 11, the latter may simultaneously be squeezed onto the sieve 71 by mechanical pressure so that parts of the smear sample are extracted directly by inserting the cotton bud 11.

Figure 4:
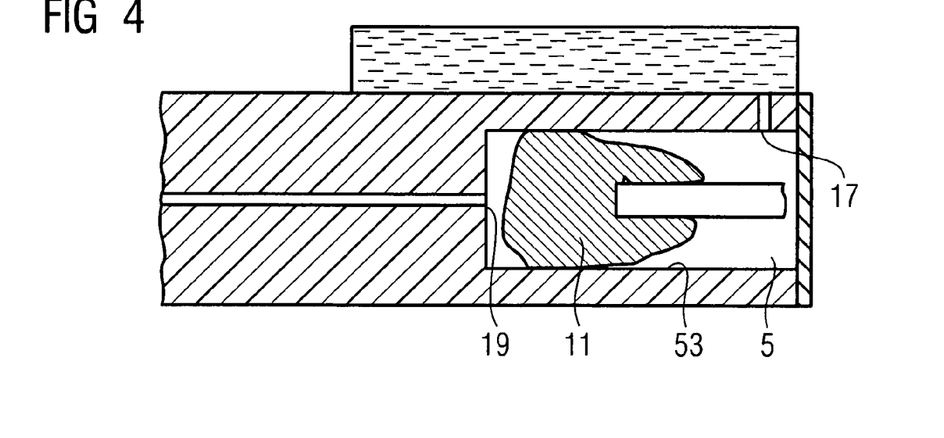

The embodiment of the invention as shown in FIG. 4 presents a device which is configured for cotton swabs, the consistency of which must be loose enough for the flushing liquid to be able to permeate the cotton bud 11. In this case, the reception chamber 5 is adapted in shape and size to the cotton bud 11 so that the flushing liquid from the inlet opening 17 can reach the outlet opening 19 essentially only by passing through the cotton bud 11. A maximally large volume of the cotton bud 11 is therefore flushed by the flushing liquid. The cotton bud 11 is in contact with the walls 53 of the reception chamber 5, so that the least possible flushing liquid reaches the outlet opening 19 past the cotton bud 11. Only by permeating the cotton bud 11, and therefore receiving the greatest possible amount of sample material, does the liquid reach the outlet opening 19.

Figure 5:
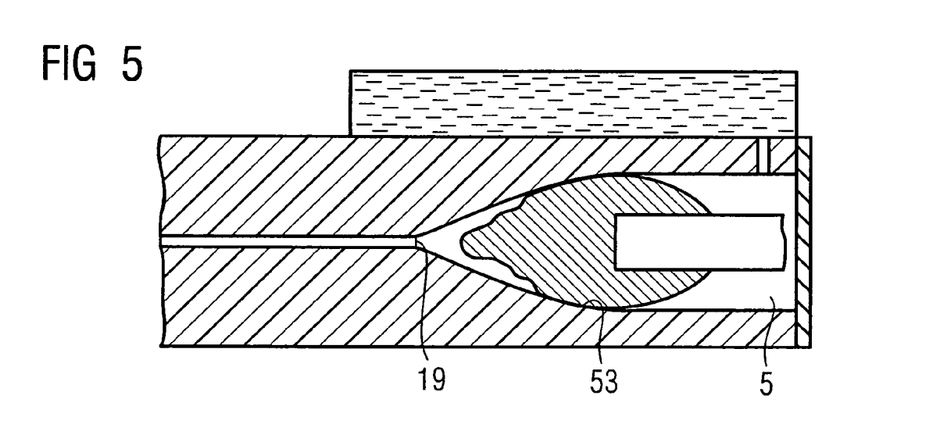

FIG. 5 shows another improved embodiment, in which the reception chamber 5 is shaped so that it tapers in the region of the outlet opening 19. When the cotton swab is inserted, the cotton bud 11 is thus pressed onto a large section of the wall 51, so as to substantially prevent the flushing liquid from flowing past the cotton bud 11 without permeating it.

Figure 6:
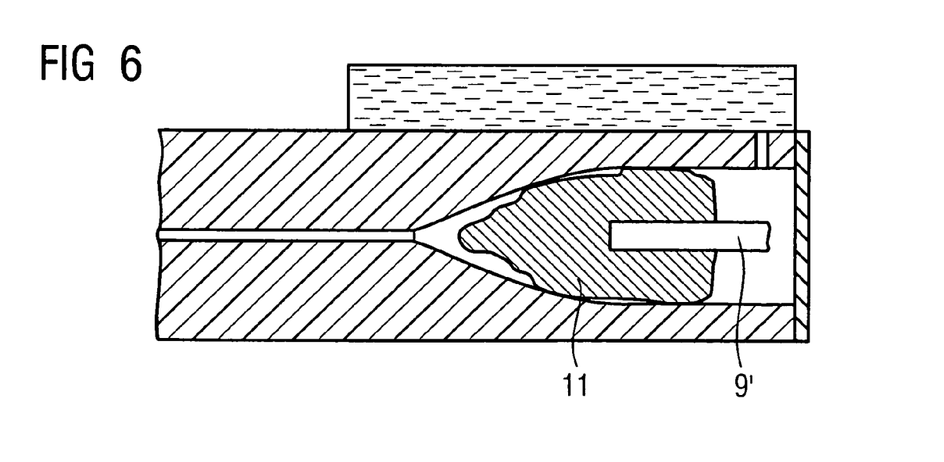

FIG. 6 shows essentially the same structure of the device, although the carrier stick 9' of the cotton bud 11 being introduced is characterized by a much smaller diameter than in the embodiment in FIG. 5. This ensures that sufficient flushing liquid can be flushed past the broken carrier stick 9' through the cotton bud 11.

Figure 7:
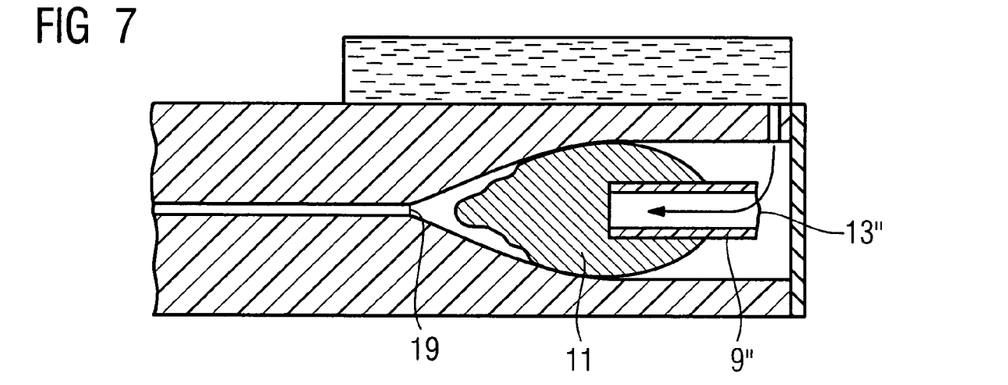

FIG. 7 shows another example embodiment, in which the broken carrier stick is hollow so that flushing liquid can also be pumped into the cotton bud 11 through the carrier stick 9" This makes it possible to transport a sufficient amount of flushing liquid through the cotton bud 11 to the outlet opening 19, and thus extract the greatest possible part of the smear sample from the sample carrier.

The corresponding carrier stick 9" may in this case be configured so that it is hollow either over its entire length or only between the weakened fracture site 13" and the cotton bud 11. A hollow carrier stick offers the advantage that the cotton bud 11 can be permeated particularly effectively by the flushing liquid.

Figure 8:
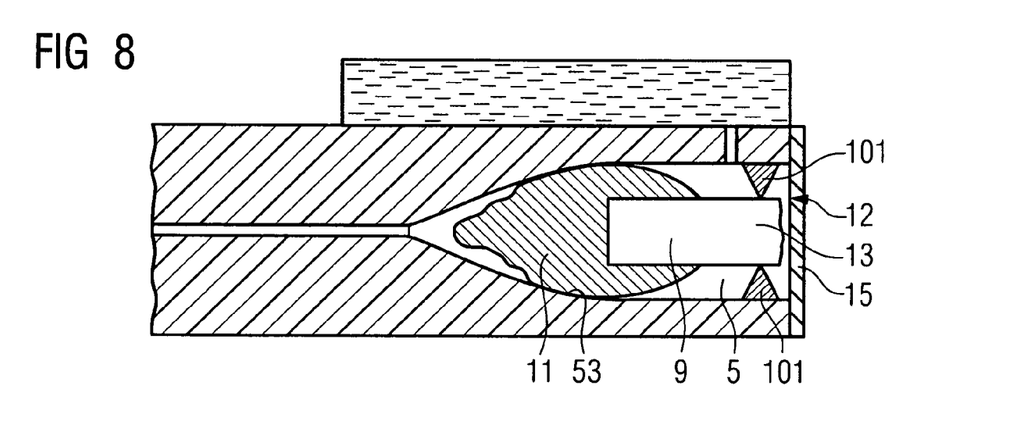

FIG. 8 shows another example embodiment in which, in the region of a reception opening 12, a plurality of projections 101 are provided shortly behind the rubber lid in the reception chamber 5. These projections 101 are sharp-edged and adapted to the diameter of the carrier stick 9, so as to help break the carrier stick 9 at the weakened fracture site 13. This simplifies the handling of the cotton swab. At the same time, the projections 101 exert a supporting and holding action on the broken carrier stick 9, so that it is fixed inside the reception chamber 5. In the embodiment of the invention as shown in FIG. 2, this also has the advantage of guaranteeing the desired distance between the cotton bud 11 and the wall 51 of the reception chamber 5.

Figure 9:
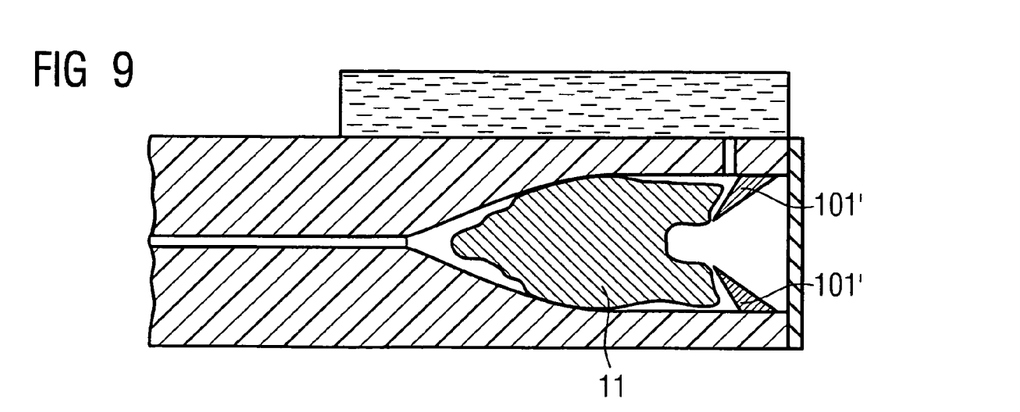

In the example embodiment represented in FIG. 9, the projections 101' are inclined somewhat in the insertion direction of the cotton swab. The cotton bud 11 can be fed through in the insertion direction, but it can no longer be retracted. In this case it is possible to obviate breaking the carrier stick since, when the carrier stick is retracted and fully removed, the projections 101' release the cotton bud 11 from it and retain it in the reception chamber.

Figure 10:
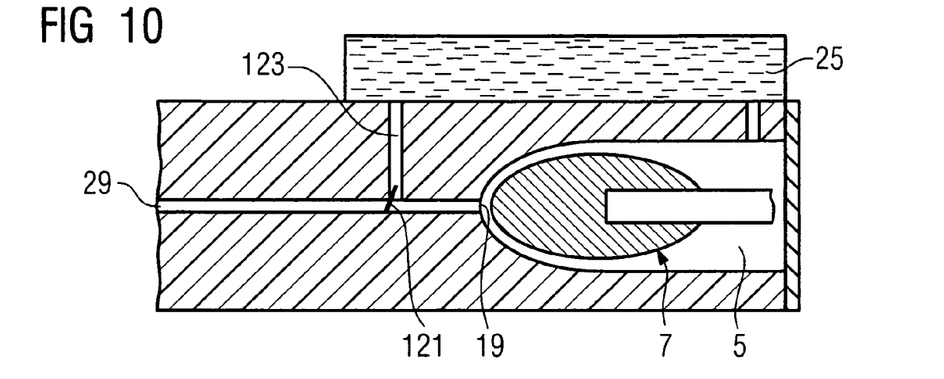

FIG. 10 shows another example embodiment, in which the microchannel 29 is connected to the liquid reservoir 25 via a valve 121 and a return flow channel 123. It is therefore possible for the flushing liquid already bound to a part of the smear sample in dissolved form to be pumped via the liquid reservoir 25 into the reception chamber 5, so that an additional part of the smear sample can be released from the sample carrier 7. By switching the valve 121 appropriately, it is possible to carry out an arbitrary number of flushing cycles. By changing the setting of the valve 121, the flushing liquid is transported through the entire microchannel 29 into the attached microfluidic system for further processing.

The release of the sample material from the sample carrier 7 may be assisted by incorporating additives into the flushing liquid. These may, for example, be detergents or enzymes which promote disintegration of the sample material. These additives may already be contained in the liquid reservoir 25, or they may be pre-stored in a solid or liquid form in the reception chamber. The latter version has the advantage that only water needs to be stored in the liquid reservoir 25. The liquid reservoir 25 can therefore be used universally, and only the reception chamber 5 has to be adapted to the respective sample type or sample carrier type.

Figure 11:
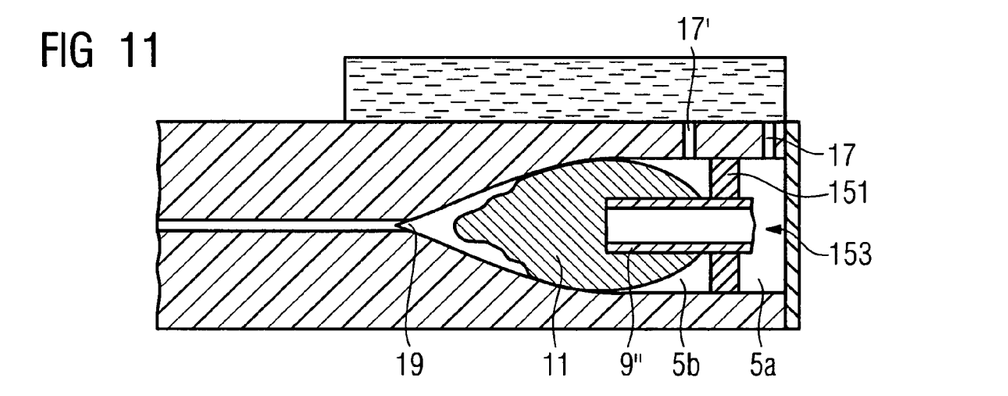

FIG. 11 shows another embodiment of the invention. A rubber ring 151, which subdivides the reception chamber 5 into two sub-chambers 5a and 5b, is arranged in the reception chamber 5. An additional inlet opening 17' is furthermore provided in the sub-chamber 5b, in which the outlet opening 19 is also arranged. The cotton swab is now introduced into the sub-chamber 5b through the rubber ring 151, which comprises an opening 153. The broken hollow carrier stick 9' is then enclosed with a form fit by the rubber ring 151. If flushing liquid is pumped into the two sub-chambers 5a and 5b via the two inlet openings 17 and 17', then the flushing liquid from the sub-chamber 5a will travel through the hollow carrier stick 9", and through the cotton bud 11 connected to it, to the outlet opening 19. The cotton bud 11 will be additionally impregnated on the sides through the inlet opening 17' arranged in the sub-chamber 5b, so that sample material will be released from the cotton.

In the case of a hollow carrier stick 9" through which the flushing liquid can flow, this prevents the sides of the cotton bud 11 from being incompletely permeated by flushing liquid. It is possible for the cotton bud 11 to be pushed through owing to the flexibility of the rubber material of the rubber ring 151, whereupon the rubber ring 151 encloses the carrier stick 9 with a form fit and retains it.

Figure 12:
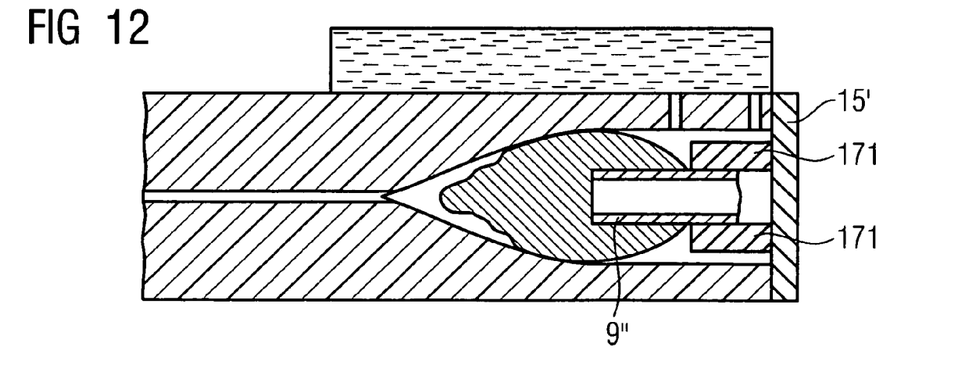

FIG. 12 shows an alternative embodiment, in which flushing liquid is prevented from being transported through the hollow carrier stick 9". In order to stop this, the rubber lid 15' carries a rubber flap 171, which encloses the broken carrier stick 9" with a form fit and thus protects it against being permeated by flushing liquid. This is important when using sample carriers with a hollow carrier stick, in which the cotton lies primarily on the side of the carrier stick. In this case, permeation through the hollow carrier stick could mean that the cotton is not impregnated sufficiently.

Figure 13:
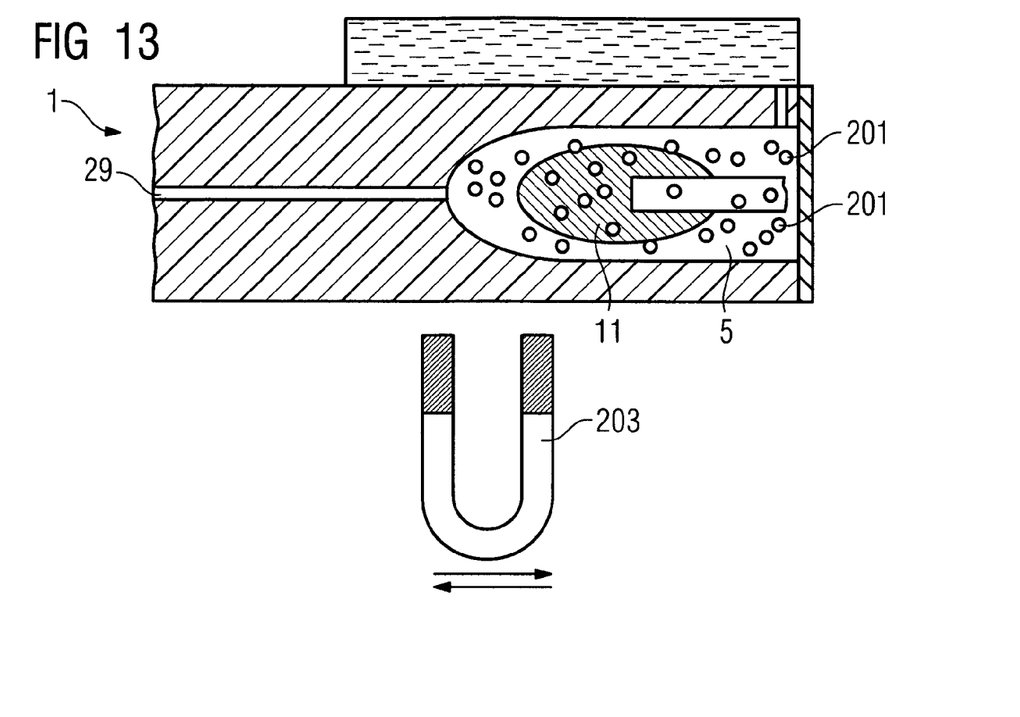

FIG. 13 shows another embodiment, in which so-called magnetic beads 201 are held in the flushing liquid or in the reception chamber. The magnetic beads 201 may, for example, be specially adapted to the sample to be processed and bind specifically to parts of the sample. If there are additionally lysis reagents in the reception chamber or in the flushing liquid, then, immediately after the sample is released from the sample carrier, it is possible to carry out cell disintegration e.g. of bacteria present in the sample and to release the DNA. This DNA may, for example, bind to a silanized surface of the magnetic beads 201 or to specific oligonucleotides which are immobilized on the surface of the magnetic beads 201.

By using a mobile permanent magnet 203 which is arranged outside the cartridge 1 in the reader, it is possible to deliver the magnetic beads 201 in a controlled way and without the other constituents of the sample through the microchannel 29 for further analysis. Contaminants remain in the reception chamber 5. The magnetic beads 201, and the lysis reagent optionally provided, may be stored either dry or in a liquid form in the reception chamber 5. In order to assist the lysis and the process of binding the DNA to the magnetic beads 201, the latter are moved to and fro in the reception chamber 5 by the mobile permanent magnet. Moving the magnetic beads 201 furthermore leads to more efficient release of the sample material from the cotton bud 11. The DNA now present in solution is bounded by specific biological molecules lying on the surfaces of the magnetic beads 201, for example antibodies or oligonucleotides, or other chemical structures, for example silane.

The parts of the sample which are to be analyzed are preferably bound to the magnetic beads 201. In subsequently performed washing processes, these can be retained by a magnetic field and thus purified. Alternatively, it is also possible for interfering constituents of the sample to be retained in the reception chamber 5, and thus not processed further with the flushing liquid and the sample constituents to be analyzed.

Figure 14:
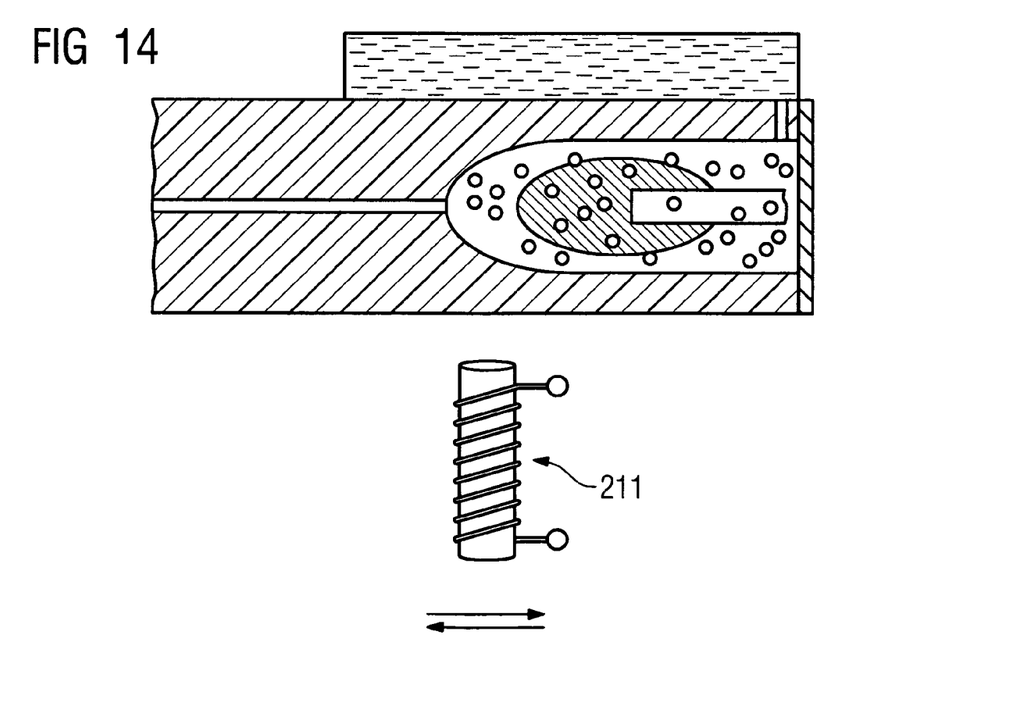

FIG. 14 shows an alternative embodiment in which a mobile electromagnet 211, which generates a magnetic field from an AC voltage, is used instead of a mobile permanent magnet.

Figure 15:
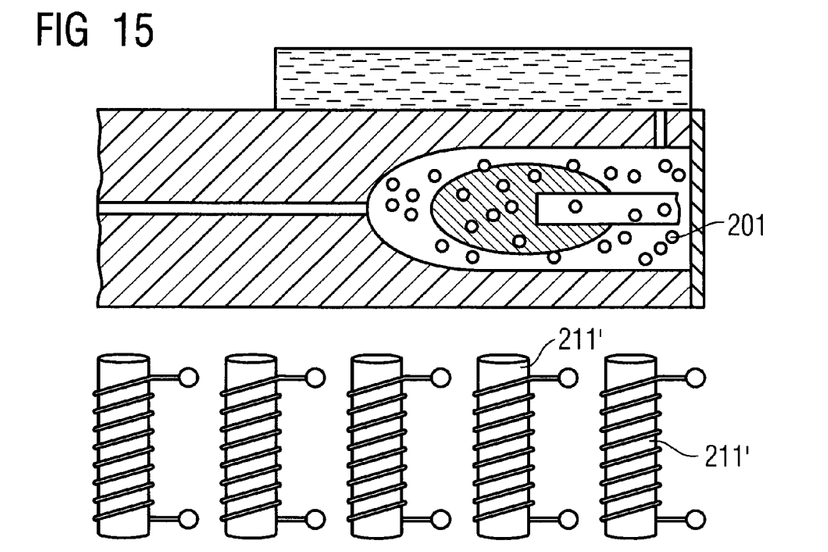

Alternatively, as shown in FIG. 15, a plurality of electromagnets 211' may be arranged next to one another so that the magnetic beads 201 can be moved to and fro, as well as through the outlet opening into the outlet channel, without moving parts.

In the embodiment shown in FIGS. 13 to 15, the liquid feed may alternatively be obviated. In this case, it is necessary that the liquid needed for the solution, for example distilled water, should be held already in the reception chamber or supplied with the sample carrier. The sample may be released from the sample carrier by the magnetic beads 201, which are set in motion by variable magnetic fields. The liquid is likewise set in motion by the movement of the magnetic beads, so that an effect comparable to stirring or centrifuging is achieved. In this case, by adding or pre-storing appropriate reagents, it is simultaneously possible to carry out cell disintegration and bind the DNA contained in the cells to the correspondingly functionalized magnetic beads 201. The DNA can then be removed from the reception chamber with the magnetic bead 201 and delivered for further analysis.

Figure 16:
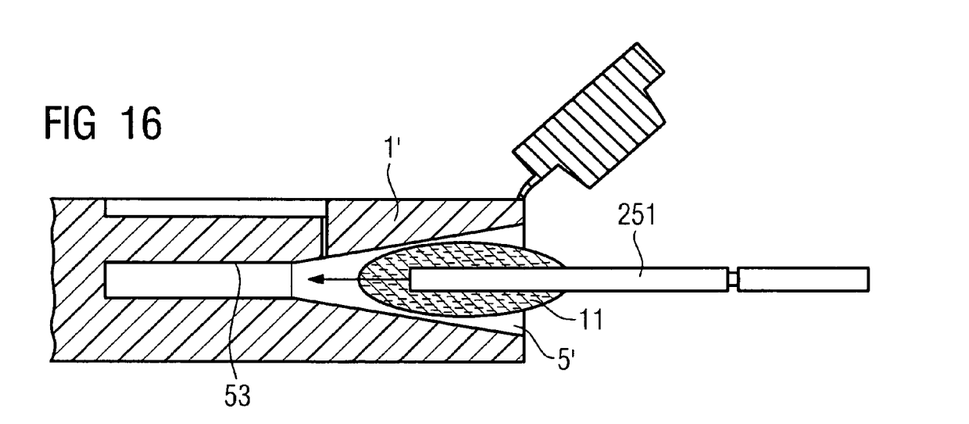

FIG. 16 shows a further embodiment of the cartridge 11, in which the reception chamber 5' has a geometry such that the spacing between the stick and the chamber wall 53' decreases continuously in a funnel shape as the cotton swab 251 is inserted, so that a very high proportion of the cotton impregnated with the smear sample is compressed and liquid with the sample correspondingly escapes from the cotton bud 11. FIG. 16 shows the reception chamber 5' in an open form when the cotton stick 251 is being inserted.

Figure 17:
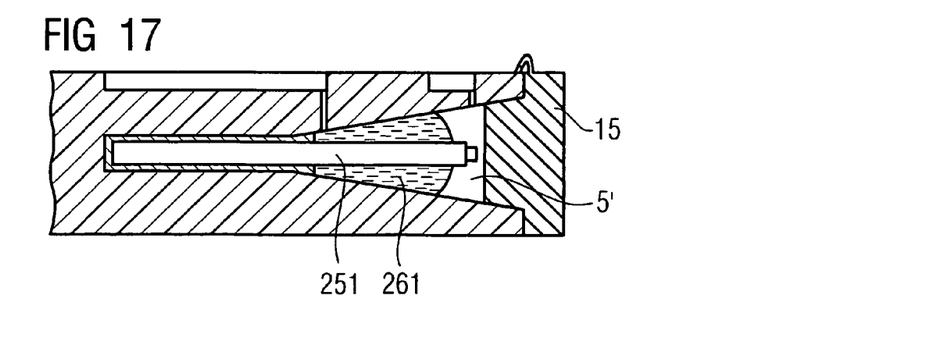

In FIG. 17, the broken cotton stick 251 has been fully inserted and the reception chamber 5' has been sealed by the rubber lid 15. The expressed liquid 261 has accumulated in the reception chamber 5', so that it can easily be removed therefrom by flushing. The reception chamber 5' contains optionally dry-stored reagents, which can break down or dissolve proteins or directly facilitate cell disintegration.

The device according to an embodiment of the invention and its various embodiments as explained above provide a substantially automated and inexpensively operating device, which makes it possible to transfer smear samples straightforwardly into a microfluidic system of a biochip cartridge. Manual working steps are substantially avoided. The device according to an embodiment of the invention may be configured both as part of an integrated analysis system and independently of the analysis system per se. Thus, it is possible for the liquid with the dissolved sample to be collected in a liquid reservoir arranged downstream of the outlet opening, from which it may for example be removed by means of a pipetting robot. The pipetting robot may transfer the correspondingly taken sample into an analyzer, where the actual analysis of the sample is carried out. Further sample analysis steps, for example cell disintegration, DNA amplification and DNA detection by means of a biochip, can then be carried out in a fully automated process.

Particularly for cartridge-based lab-on-a-chip systems, the device according to an embodiment of the invention offers the advantage that except for introducing the smear sample carrier into the cartridge, no more manual working steps are necessary. The extraction of the smear sample and the transfer into the fluidic system of the cartridge thus take place fully automatically, and initial processing steps such as lysis or binding to magnetic beads for further transporting parts of the sample may be carried out inside the reception chamber for the sample carrier.

The described example embodiments relate to the extraction of a smear sample, which contains DNA to be detected. In principle, various types of target molecules may be extracted with the smear sample or from the smear sample by the device according to the invention and its example embodiments. These may, for example, be proteins.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A device for extracting a smear sample, comprising:
   a cavity, into which a sample carrier carrying a smear sample is introducible, wherein at least one holding part is arranged in the cavity, the holding part including at least one recess acutely converging essentially in an insertion direction of the sample carrier;
   at least one liquid feed connected to the cavity, through which liquid is introducible into the cavity;
   at least one liquid discharge connected to the cavity, through which liquid is removable from the cavity; and
   an interface to a microfluidic system, into which liquid is transferable.

2. The device as claimed in claim 1, wherein at least one of the at least one liquid feed and the at least one liquid discharge comprises at least one microchannel.

3. The device as claimed in claim 1, wherein the cavity comprises a reception opening configured to receive the sample carrier and a stopper, the reception opening being liquid-tightly sealable using the stopper.

4. The device as claimed in claim 3, wherein the reception opening is germ-tightly sealable by the stopper.

5. The device as claimed in claim 3, wherein the stopper is configured to automatically seal the cavity after the sample carrier is introduced to the cavity.

6. The device as claimed in claim 1, wherein the liquid feed comprises at least one liquid reservoir, connectible at least temporarily to the cavity and from which, when it is connected to the cavity, a liquid held in the liquid reservoir is introducible into the cavity.

7. The device as claimed in claim 6, wherein the liquid consists of distilled water, to which substances that assist release of the smear sample from the sample carrier are added.

8. The device as claimed in claim 1, wherein the cavity comprises an inlet opening and an outlet opening, via which the liquid feed and the liquid discharge are respectively fluidly connected to the cavity.

9. The device as claimed in claim 8, wherein the inlet opening and the outlet opening are arranged so that, when the sample carrier is introduced, a maximally large section of the sample carrier lies between the inlet opening and the outlet opening.

10. The device as claimed in claim 8, wherein the cavity is matched to a shape and size of the sample carrier so that, when the sample carrier is introduced into the cavity, between a wall of the cavity and the sample carrier there is a spacing dimensioned such that liquid is transportable past the sample carrier from the inlet opening to the outlet opening.

11. The device as claimed in claim 1, wherein
    the holding part is essentially shaped to correspond to at least a part of the sample carrier and the sample carrier is insertable into the holding part, the holding part having a spacing from the wall of the cavity dimensioned so that liquid can travel from the inlet opening to the outlet opening, and
    the holding part comprises openings which facilitate contact between the liquid and the sample carrier, when the sample carrier is inserted into the holding part.

12. The device as claimed in claim 1, wherein the holding part comprises a sieve-like structure.

13. The device as claimed in claim 1, wherein the cavity includes a reception opening, and
    the holding part is arranged in a region of the reception opening and is configured to prevent parts of the sample carrier, which carry the smear sample, from being removed from the cavity.

14. The device as claimed in claim 8, wherein the cavity is matched to a shape and size of the sample carrier so that, when the sample carrier is introduced into the cavity, between a wall of the cavity and the sample carrier there is a spacing dimensioned such that the liquid can travel from the inlet opening to the outlet opening only by passing through the sample carrier.

15. The device as claimed in claim 8, wherein the cavity has a tapering shape in the region of the outlet opening.

16. A device for extracting a smear sample, comprising:
a cavity, into which a sample carrier carrying a smear sample is introducible;
at least one liquid feed connected to the cavity, through which liquid is introducible into the cavity;
at least one liquid discharge connected to the cavity, through which liquid is removable from the cavity. wherein the cavity includes an outlet opening via which the liquid discharge is fluidly connected to the cavity;
an interface to a microfluidic system, into which liquid is transferable; and
a separating unit, which subdivides the cavity into at least two sub-cavities, arranged in the cavity,
wherein each of the sub-cavities includes an inlet opening, connected to the liquid feed,
a reception opening of the cavity and the outlet opening are in different sub-cavities,
the separating unit includes an access opening, through which the sample carrier is introduced at least partially into the sub-cavity with the outlet opening.

17. The device as claimed in claim 8, wherein the outlet opening is connectible outside the cavity selectively to at least one of the inlet opening and the liquid discharge.

18. The device as claimed in claim 17, wherein the outlet opening is connected to a channel system, the channel system comprising at least one valve via which the outlet opening is selectively connectible to at least one of the inlet opening and the liquid discharge.

19. A device for extracting a smear sample, comprising:
a cavity, into which a sample carrier carrying a smear sample is introducible;
at least one liquid feed connected to the cavity, through which liquid is introducible into the cavity, wherein the cavity includes an inlet opening via which the liquid feed is fluidly connected to the cavity;
at least one liquid discharge connected to the cavity, through which liquid is removable from the cavity. wherein the cavity includes an outlet opening via which the liquid discharge is fluidly connected to the cavity; and
an interface to a microfluidic system, into which liquid is transferable,
wherein in a region of the outlet opening, the cavity is tapered so that, when the sample carrier is introduced, the sample carrier is mechanically deformed such that the smear sample at least partially escapes.

20. The device as claimed in claim 1, wherein treatment reagents for the sample are stored in the cavity.

21. The device as claimed in claim 20, wherein the treatment reagents comprise means for carrying out cell disintegration.

22. The device as claimed in claim 20, wherein the treatment reagents comprise means for binding at least parts of the sample.

23. The device as claimed in claim 22, wherein the means for binding at least parts of the sample are configured as magnetic beads, and wherein the device comprises a magnet unit configured to move the magnetic beads.

24. A method for extracting a smear sample, comprising:
introducing a sample carrier carrying a smear sample into a cavity of a device;
introducing liquid into the cavity through at least one liquid feed connected to the cavity, wherein the introduction of the liquid into the cavity is triggered automatically by closing a stopper;
releasing at least a portion of the smear sample from the sample carrier using the liquid; and
at least partially removing the liquid and the smear sample through at least one liquid discharge connected to the cavity.

25. A method for extracting a smear sample, comprising:
introducing a sample carrier carrying a smear sample into a cavity of a device;
introducing liquid into the cavity through at least one liquid feed connected to the cavity:
releasing at least a portion of the smear sample from the sample carrier using the liquid; and
at least partially removing the liquid and the smear sample through at least one liquid discharge connected to the cavity,
wherein the liquid is transported several times through the cavity, each time being transported from an outlet opening back to an inlet opening.

26. The method as claimed in claim 24, further comprising disintegrating cells in the smear sample after releasing the portion of the smear sample.

27. A method for extracting a smear sample, comprising:
introducing a sample carrier carrying a smear sample into a cavity of a device;
introducing liquid into the cavity through at least one liquid feed connected to the cavity:
releasing at least a portion of the smear sample from the sample carrier using the liquid;
disintegrating cells in the released smear sample; and
at least partially removing the liquid and the released smear sample through at least one liquid discharge connected to the cavity, wherein target molecules contained in the cells are bound to functionalized magnetic beads and transported into the liquid discharge via a magnet unit.

28. The device as claimed in claim 2, wherein the cavity comprises a reception opening configured to receive the sample carrier and a stopper, the reception opening being liquid-tightly sealable using the stopper.

29. The device as claimed in claim 28, wherein the reception opening is germ-tightly sealable by the stopper.

30. The device as claimed in claim 21, wherein the treatment reagents comprise means for binding at least parts of the sample.

31. The method as claimed in claim 24, wherein the liquid is transported several times through the cavity, each time being transported from an outlet opening back to an inlet opening.

32. The device as claimed in claim 16, wherein the sample carrier is at least partially enclosed essentially with a form fit by the access opening so that liquid from the cavity with the reception opening is transportable to the outlet opening only by passing through the sample carrier.

* * * * *